(12) United States Patent
Lagatol et al.

(10) Patent No.: US 7,163,692 B2
(45) Date of Patent: Jan. 16, 2007

(54) FOAM ENHANCEMENT BY CATIONIC POLYMERS

(75) Inventors: Shauna Mary Lagatol, Westwood, NJ (US); Jesus Antonio Urbaez, Waterbury, CT (US); Paul Roland Bergquist, Southport, CT (US)

(73) Assignee: Unilever Home & Personal Care USA, Division of Conopco, Inc., Greenwich, CT (US)

(*) Notice: Subject to any disclaimer, the term of this patent is extended or adjusted under 35 U.S.C. 154(b) by 581 days.

(21) Appl. No.: 10/462,181

(22) Filed: Jun. 16, 2003

(65) Prior Publication Data

US 2004/0126411 A1 Jul. 1, 2004

(51) Int. Cl.
*A61F 13/00* (2006.01)
*A61K 6/00* (2006.01)
*A61K 9/14* (2006.01)
*C11D 17/00* (2006.01)

(52) U.S. Cl. .................... 424/443; 424/401; 424/489; 510/295; 510/297; 510/439

(58) Field of Classification Search ............... 510/295, 510/297, 439; 424/443, 401, 489

See application file for complete search history.

(56) References Cited

U.S. PATENT DOCUMENTS

| 5,417,965 A | 5/1995 | Janchitraponvej et al. |
| 5,951,991 A | 9/1999 | Wagner et al. |
| 5,980,931 A | 11/1999 | Fowler et al. |
| 6,063,390 A | 5/2000 | Farrell et al. |
| 2002/0006886 A1* | 1/2002 | Beerse et al. ............... 510/295 |

FOREIGN PATENT DOCUMENTS

| EP | 0 688 901 | 12/1995 |
| FR | 2 276 030 | 0/1974 |
| WO | 99/55303 | 11/1999 |

* cited by examiner

*Primary Examiner*—Shengjun Wang
*Assistant Examiner*—Yong S. Chong
(74) *Attorney, Agent, or Firm*—Milton L. Honig

(57) ABSTRACT

A substantially dry personal care cleansing article is provided which includes a water-insoluble substrate and associated with the substrate a personal care cleansing composition. The latter includes at least one lathering surfactant and at least about 2% of a cationic polymer. The composition has an average particle size ranging from about 75 to about 900 micron. The cationic polymer improves the rapidity and duration of foam formation when the article is wetted with water to activate the surfactant.

7 Claims, No Drawings

FOAM ENHANCEMENT BY CATIONIC POLYMERS

BACKGROUND OF THE INVENTION

1. Field of the Invention

The invention relates to a personal cleansing article in wipe format having improved foaming properties.

2. The Related Art

Personal cleansing and conditioning products have traditionally been marketed in a variety of forms such as bars, liquids and gels. These formats have attempted to satisfy a number of criteria for acceptability to consumers. Among them are cleansing effectiveness, skin feel, mildness and lather volume. Ideal products should gently cleanse the skin or hair, cause little or no irritation, and not leave the skin or hair overly dry after frequent use.

A series of granted and pending patent applications have been published by Procter & Gamble describing disposable personal cleansing products addressing many of the aforementioned functionality concerns. These products are substantially dry articles having deposited onto a woven or non-woven cloth a cleansing composition of surfactant, structurant, skin conditioning agent and other performance ingredients. The technology is described in the following patents.

U.S. Pat. No. 5,951,991 (Wagner et al.) focuses on providing the substrate with a conditioning emulsion separately impregnated from the lathering surfactant onto the cloth substrate. U.S. Pat. No. 5,980,931 (Fowler et al.) emphasizes impregnation of oil soluble conditioning agents. WO 99/55303 (Albacarys et al.) describes skin care actives formulated with the cleansing composition.

Another approach to cleansing is reported in U.S. Pat. No. 6,063,390 (Farrell et al.). Therein are disclosed cosmetic wiping articles based upon a pouch formed by at least one water permeable wall and containing an effervescent cleanser composition in the form of an anhydrous dry powder. Effervescence and foaming is achieved by a powdered combination of alkaline material, acid material and a surfactant. A variety of skin benefit agents can be included to improve afterfeel properties. Illustrative are deposition aids such as cationic guar gums including guar hydroxypropyltrimonium chloride in amounts ranging up to about 1% by weight.

A general problem with dry cleansing wipe articles is a tendency for foam not to last too long. Systems have been sought which would extend the foam phenomena.

SUMMARY OF THE INVENTION

A substantially dry personal care cleansing article is provided which includes:

(i) a water insoluble substrate;

(ii) a personal care composition adjacent the substrate, which includes:

(a) from about 0.5 to about 60% of at least one lathering surfactant by weight of the composition;

(b) from about 2 to about 15% of a cationic polymer by weight of the composition; and (c) a carrier for the lathering surfactant and cationic polymer, the composition having an average particle size ranging from about 75 to about 900 micron.

DETAILED DESCRIPTION OF THE INVENTION

Now it has been discovered that cationic polymers can extend foam duration in substantially dry lathering wiping articles. The improvement is achieved with at least about 2% cationic polymer by weight of the personal care composition, these levels being significantly higher than those normally utilized in such systems. Typical levels in commercial products are kept considerably below 1%, usually about 0.3–0.5% and function as deposition aids or conditioners rather than as foam enhancing agents. Further, it has been found that the compositions must have an average particle size within the range from about 75 to about 900 micron, preferably from about 100 to about 500 micron, optimally from about 180 to about 400 micron.

Thus, an important element of the personal care composition component of wiping articles according to the present invention is that of a cationic polymer. Amounts of the polymer may range from about 2% to about 15%, preferably from about 3% to about 10%, optimally from about 4 to about 8% by weight of the personal care composition.

Cationic polymers suitable for purposes of this invention may be selected from cellulose derived and synthetic polymers.

Cellulose Derived Polymers: By cellulose derived polymers is meant any polymer containing a cellulose backbone, i.e. a polysaccharide. In these cellulose derived polymers, the hydroxy groups of the cellulose polymer have been hydroxyalkylated (preferably hydroxyethylated or hydroxypropylated) to form a hydroxyalkylated cellulose which is then further modified with a cationic quaternary ammonium or protonated ammonium group. Preferred cationic modifying groups are those having at least one $C_{10-20}$ alkyl chain and two shorter alkyl chains (i.e. $C_1$ or $C_2$) on the nitrogen. The substituent on the cellulose polymer can thus be depicted as —(X)NRR'R" wherein X is hydroxyalkyl (preferably —OCH$_2$CH$_2$— or —OCH$_2$CHOHCH$_2$—), R and R' are methyl or ethyl, and R" is $C_{10-20}$ alkyl [preferably lauryl, stearyl, or cocoyl (i.e. a mixture of alkyl groups derived from coconut oil)]. In other alternative structures it has been found that when R, R', and R" are all methyl (i.e. the trimonium group) that useful cellulose polymers are also obtained. In yet other alternative structures the cationic substituent on the cellulose contains both a hydroxyethyl and a hydroxypropyl group such that the moiety can be depicted as —(OCH$_2$CH$_2$O)—CH$_2$CHOHCH$_2$NRR'R" wherein R, R', and R" are methyl or ethyl, and R" is $C_{10-20}$ alkyl [preferably lauryl, stearyl, or cocoyl (i.e. a mixture of alkyl groups derived from coconut oil)], or alternatively wherein R, R', and R" are all methyl (i.e. the trimonium group).

Commercially available cationic modified celluloses include: laurdimonium hydroxyethyl cellulose (wherein in the above formula X is —OCH$_2$CH$_2$—, R and R' are methyl, and R" is lauryl), and steardimonium hydroxyethyl cellulose (wherein in the above formula X is —OCH$_2$CH$_2$—, R and R' are methyl, and R" is stearyl). These materials are known by the trade names CRODACEL QL and CRODACEL AS which are all commercially available from Croda Corp. Another highly useful cationic cellulose is laurdimonium hydroxypropyl oxyethyl cellulose (wherein the modifying group on the cellulose is —(OCH$_2$CH$_2$O)—CH$_2$CHOHCH$_2$NRR'R", wherein R, R' are methyl and R" is lauryl), which is commercially available as CRODACEL QL SPECIAL, from Croda Corp. Other useful cationic celluloses are available from Amerchol Corp. (Edison, N.J., USA), as POLYMER JR LR, and LK series which are salts of hydroxyethyl cellulose reacted with trimethyl ammonium substituted epoxide, referred to in the industry (CTFA) as Polyquaternium 10; and the polymeric quaternary ammonium salts of hydroxyethyl cellulose reacted with lauryl dimethyl ammonium-substituted epoxide, referred to in the industry (CTFA) as Polyquaternium 24 which are available from Amerchol Corp. (Edison, N.J., USA) under the tradename POLYMER LM-200.

Other suitable cationic polymers that can be used herein include cationic guar gum derivatives, such as the cationic polygalactomannan gum derivative described in U.S. Pat. No. 4,298,494 which are commercially available under the trademark JAGUAR; the hydroxypropyltrimethylammonium derivative of guar gum which is commercially available under the trademark JAGUAR C-13S and JAGUAR C-17 (CTFA designation guar hydroxypropyltrimonium chloride); and the hydroxypropylated cationic guar derivative known as JAGUAR C-16. Other materials include quaternary nitrogen-containing cellulose ethers (e.g., as described in U.S. Pat. No. 3,962,418) and copolymers of etherified cellulose and starch (e.g., as described in U.S. Pat. No. 3,958,581).

Related to these cellulose polymers are ones having backbones that are derived from other sugars (or their related acids, alcohols, amines, etc), e.g. galactose, mannose, arabinose, xylose, fructose, fructose, glucosamine, galactosamine, glucuronic acid, galacturonic acid, 5 or 6 membered ring polyalcohols, and mixtures therof.

Synthetic Polymers: Suitable cationic polymers in this category include copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone and vinyl pyrrolidone. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of polyvinyl acetate), maleic andhydride, propylene glycol, and ethylene glycol.

The cationic amines can be primary, secondary, or tertiary amines, depending upon the particular species. In general, secondary and tertiary amines, especially tertiary amines, are preferred.

Amine-substituted vinyl monomers can be polymerized in the amine form, and then optionally can be convered to ammonium by a quaternization reaction. Amines can also be similarly quaternized subsequent to formation of the polymer. For example, tertiary amine functionalities can be quaternized by reaction with a salt of the formula R'X wherein R' is a short chain alkyl, preferably a $C_7$–$C_{10}$ alkyl, more preferably a $C_1$–$C_3$ alkyl, and X is an anion which forms a water soluble salt with the quaternized ammonium.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$–$C_3$ alkyls, more preferably $C_1$ and $C_2$ alkyls.

Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_{12}$–$C_{13}$, alkyls.

The cationic polymers hereof can comprise mixtures of monomer units derived from amine- and/or quaternary ammonium-substituted monomer and/or compatible spacer monomers.

Suitable synthetic cationic polymers include copolymers of 1-vinyl-2-pyrrolidone and 1-vinyl-3-methylimidazolium salt (e.g., chloride salt) (referred to as Polyquaternium-16), commercially available from BASF Wyandotte Corp. (Parsippany, N.J., USA) under the LUVIQUAT tradename (e.g., LUVIQUAT FC 370); copolymers of 1-vinyl-2-pyrrolidone and dimethylaminoethyl methacrylate (referred to as Polyquaternium-11) commercially available from ISP Corporation (Wayne, N.J., USA) under the GAFQUAT tradename (e.g., GAFQUAT 755 and 755N); cationic diallyl quaternary ammonium-containing polymers, including, for example, dimethyldiallylammonium chloride homopolymer and copolymers of acrylamide and dimethyldiallylammonium chloride (referred to as Polyquaternium 6 and Polyquaternium 7, respectively), the mineral acid salts of amino-alkyl esters of homo- and co-polymers of unsaturated carboxylic acids having from 3 to 5 carbon atoms; the graft cationic copolymer containing N-vinylpyrrolidone, dimethylaminoethyl methacrylate and polyethylene glycol; the high molecular weight cationic polymers designated as Quaternium-40 (a highly charged cationic dimethyldiallylammonium chloride homopolymer) and Quaternium-41 (a highly charged cationic copolymer prepared with dimethyldiallylammonium chloride and acrylamide), which are commercially available under the trademarks MERQUAT 100 and MERQUAT 550 from Merck & Com., Inc.; and mixtures thereof.

A further element of compositions according to the present invention is that of a lathering surfactant. By a "lathering surfactant" is meant a surfactant, which when combined with water and mechanically agitated generates a foam or lather. Preferably, these lathering surfactants should be mild, which means that they must provide sufficient cleansing or detersive benefits but not overly dry the skin or hair.

The articles of the present invention typically include at least one lathering surfactant in an amount from about 0.5% to about 60%, preferably from about 0.75% to about 40%, and more preferably from about 1% to about 20%, based on the weight of the composition.

A wide variety of lathering surfactants are useful herein and include those selected from the group consisting of anionic, nonionic, cationic, amphoteric and lathering surfactant mixtures thereof.

Among the anionic lathering surfactants useful herein are the following non-limiting examples which include the classes of:

(1) Alkyl benzene sulfonates in which the alkyl group contains from 9 to 15 carbon atoms, preferably 11 to 14 carbon atoms in straight chain or branched chain configuration. Especially preferred is a linear alkyl benzene sulfonate containing about 12 carbon atoms in the alkyl chain.

(2) Alkyl sulfates obtained by sulfating an alcohol having 8 to 22 carbon atoms, preferably 12 to 16 carbon atoms. The alkyl sulfates have the formula $ROSO_3^-M^+$ where R is the $C_{8-22}$ alkyl group and M is a mono- and/or divalent cation.

(3) Paraffin sulfonates having 8 to 22 carbon atoms, preferably 12 to 16 carbon atoms, in the alkyl moiety. These surfactants are commercially available as Hostapur SAS from Hoechst Celanese.
(4) Olefin sulfonates having 8 to 22 carbon atoms, preferably 12 to 16 carbon atoms. Most preferred is sodium $C_{14}$–$C_{16}$ olefin sulfonate, available as Bioterge AS 40®
(5) Alkyl ether sulfates derived from an alcohol having 8 to 22 carbon atoms, preferably 12 to 16 carbon atoms, ethoxylated with less than 30, preferably less than 12, moles of ethylene oxide. Most preferred is sodium lauryl ether sulfate formed from 2 moles average ethoxylation, commercially available as Standopol ES-2®.
(6) Alkyl glyceryl ether sulfonates having 8 to 22 carbon atoms, preferably 12 to 16 carbon atoms, in the alkyl moiety.
(7) Fatty acid ester sulfonates of the formula: $R^1CH(SO_3\text{-}M+)CO_2R^2$ where $R^1$ is straight or branched alkyl from about $C_8$- to $C_{18}$, preferably $C_{12}$ to $C_{16}$, and $R^2$ is straight or branched alkyl from about $C_1$ to $C_6$, preferably primarily $C_1$, and M+ represents a mono- or divalent cation.
(8) Secondary alcohol sulfates having 6 to 18, preferably 8 to 16 carbon atoms.
(9) Fatty acyl isethionates having from 10 to 22 carbon atoms, with sodium cocoyl isethionate being preferred.
(10) Dialkyl sulfosuccinates wherein the alkyl groups range from 3 to 20 carbon atoms each.
(11) Alkanoyl sarcosinates corresponding to the formula $RCON(CH_3)CH_2CH_2CO_2M$ wherein R is alkyl or alkenyl of about 10 to about 20 carbon atoms and M is a water-soluble cation such as ammonium, sodium, potassium and trialkanolammonium. Most preferred is sodium lauroyl sarcosinate.
(12) Alkyl lactylates wherein the alkyl groups range from 8 to 12 carbon atoms, with sodium lauroyl lactylate sold as Pationic 138C® available from the Patterson Chemical Company as the most preferred.
(13) Taurates having from 8 to 16 carbon atoms, with cocoyl methyl taurate being preferred.

Nonionic lathering surfactants suitable for the present invention include $C_{10}$–$C_{20}$ fatty alcohol or acid hydrophobes condensed with from 2 to 100 moles of ethylene oxide or propylene oxide per mole of hydrophobe; $C_2$–$C_{10}$ alkyl phenols condensed with from 2 to 20 moles of alkylene oxides; mono- and di-fatty acid esters of ethylene glycol such as ethylene glycol distearate; fatty acid monoglycerides; sorbitan mono- and di-$C_8$–$C_{20}$ fatty acids; and polyoxyethylene sorbitan available as Polysorbate 80 and Tween 80® as well as combinations of any of the above surfactants.

Other useful nonionic surfactants include alkyl polyglucosides, saccharide fatty amides (e.g. methyl gluconamides) as well as long chain tertiary amine oxides. Examples of the latter category are:
dimethylododecylamine oxide, oleyldi(2-hydroxyethyl) amine oxide, dimethyloctylamine oxide, dimethyldecylamine oxide, dimethyltetradecylamine oxide, di(2-hydroxyethyl)tetradecylamine oxide, 3-didodecyloxy-2-hydroxypropyldi(3-hydroxypropyl)amine oxide, and dimethylhexadecylamine oxide.

Amphoteric lathering surfactants useful for the present invention include aliphatic secondary and tertiary amines, preferably wherein the nitrogen is in a cationic state, in which the aliphatic radicals can be straight or branched chain and wherein one of the radicals contains an ionizable water solubilizing group such as carboxy, sulphonate, sulphate, phosphate or phosphonate. Illustrative substances are cocamidopropyl betaine, cocamphoacetate, cocamphodiacetate, cocamphopropionate, cocamphodipropionate, cocamidopropyl hydroxysultaine, cetyl dimethyl betaine, cocamidopropyl PG-dimonium chloride phosphate, coco dimethyl carboxymethyl betaine, cetyl dimethyl betaine and combinations thereof.

A necessary element of the present invention is that of a water insoluble substrate. By "water insoluble" is meant the substrate does not dissolve or readily break apart upon immersion in water. A wide variety of materials can be used as the substrate. The following non-limiting characteristics may be desirable: (i) sufficient wet strength for use, (ii) sufficient abrasivity, (iii) sufficient loft and porosity, (iv) sufficient thickness, and (v) appropriate size.

Non-limiting examples of suitable insoluble substrates which meet the above criteria include non-woven substrates, woven substrates, hydro-entangled substrates, air entangled substrates and the like. Preferred embodiments employ non-woven substrates since they are economical and readily available in a variety of materials. By non-woven is meant that the layer is comprised of fibers which are not woven into a fabric but rather are formed into a sheet, particularly a tissue. The fibers can either be random (i.e., randomly aligned) or they can be carded (i.e. combed to be oriented in primarily one direction). Furthermore, the non-woven substrate can be composed of a combination of layers of random and carded fibers.

Non-woven substrates may be comprised of a variety of materials both natural and synthetic. By natural is meant that the materials are derived from plants, animals, insects or byproducts. By synthetic is meant that the materials are obtained primarily from various man-made materials or from material that is usually a fibrous web comprising any of the common synthetic or natural textile-length fibers, or mixtures thereof.

Non-limiting examples of natural materials useful in the present invention are silk fibers, keratin fibers and cellulosic fibers. Non-limiting examples of keratin fibers include those selected from the group consisting of wool fibers, camel hair fibers, and the like. Non-limiting examples of cellulosic fibers include those selected from the group consisting of wood pulp fibers, cotton fibers, hemp fibers, jute fibers, flax fibers, and mixtures thereof.

Non-limiting examples of synthetic materials useful in the present invention include those selected from the group consisting of acetate fibers, acrylic fibers, cellulose ester fibers, modacrylic fibers, polyamide fibers, polyester fibers, polyolefin fibers, polyvinyl alcohol fibers, rayon fibers and mixtures thereof. Examples of some of these synthetic materials include acrylics such as Acrilan®, Creslan®, and the acrylonitrile-based fiber, Orlon®; cellulose ester fibers such as cellulose acetate, Arnel®, and Acele®; polyamides such as Nylons (e.g., Nylon 6, Nylon 66, and Nylon 610); polyesters such as Fortrel®, Kodel®, and Dacron®; polyolefins such as polypropylene, polyethylene; polyvinyl acetate fibers and mixtures thereof.

Non-woven substrates made from natural materials consist of webs or sheets most commonly formed on a fine wire screen from a liquid suspension of the fibers.

Substrates made from natural materials useful in the present invention can be obtained from a wide variety of commercial sources. Non-limiting examples of suitable commercially available paper layers useful herein include Airtex®, an embossed airlaid cellulosic layer available from James River Corporation, Green Bay, Wis.; and Walkisoft®, an embossed airlaid cellulosic available from Walkisoft U.S.A., Mount Holly, N.C.

Non-woven substrates made from synthetic material useful in the present invention can also be obtained form a wide variety of commercial sources. Non-limiting examples of suitable non-woven layer materials useful herein include HFE-40-047, an apertured hydroentangled material containing about 50% rayon and 50% polyester available from Vertec, Inc., Walpole, Mass.; HEF 140-102, an apertured hydro-entangled material containing about 50% rayon and 50% polyester available from Veratec, Inc., Walpole, Mass.; Novenet® 149-191, a thermo-bonded grid patterned material containing about 69% rayon, about 25% polypropylene, and about 6% cotton available from Veratec, Inc., Walpole, Mass.; HEF Nubtex® 149-801, a nubbed, apertured hydro-entangled material, containing about 100% polyester available from Veratec, Inc. Walpole, Mass.; Keybak® 951V, a dry formed apertured material, containing about 75% rayon and about 25% acrylic fibers available from Chicopee Corporation, New Brunswick, N.J.; Keybak® 1368, an apertured material, containing about 75% rayon and about 5% polyester available from Chicopee Corporation, New Brunswick, N.J.; Duralace® 1236, an apertured, hydro-entangled material, containing about 100% rayon available from Chicopee Corporation, New Brunswick, N.J.; Duralace® 5904, an apertured, hydro-entangled material, containing about 100% polyester available from Chicopee Corporation, New Brunswick, N.J.; Sontara® 8868, a hydro-entangled material, containing about 50% cellulose and about 50% polyester available from Dupont Chemical Corp.

The water insoluble substrates of the present invention can comprise two or more layers, each having a different texture and abrasiveness. The differing textures can result from the use of different combinations of materials or from the use of a substrate having a more abrasive side for exfoliation and a softer, absorbent side for gentle cleansing. In addition, separate layers of the substrate can be manufactured to have different colors, thereby helping the user to further distinguish the surfaces.

The amount of personal care composition relative to the substrate may range in weight from about 20:1 to 1:20, preferably from 10:1 to about 1:10 and optimally from about 2:1 to about 1:2 by weight.

Although the present invention can operate with single substrate wiping articles, the preferred use is with a sachet enclosing an effervescent personal care cleansing composition. The latter is in the form of a substantially anhydrous powder including an alkaline material and an acid material which together when wetted with water liberate carbon dioxide. Formulated with the powder is at least one lathering surfactant and the cationic polymer which enhances rapidity and duration of foaming.

In this preferred embodiment, the sachet in a form of a pouch is constructed of at least one water permeable wall. A preferred embodiment of the pouch includes one wall which is formed of a spunlace substrate and a second wall formed of a meltblown composite substrate, the latter being bonded to a high loft sheet. The powdered effervescent personal care cleansing composition is dosed into the pouch and the walls ultrasonically sealed to ensure no loss of the powdered composition. Copious foam is generated when the pouch is wetted with water, much in the same manner as a toilet bar is lathered.

When the personal care composition is an effervescent system, there will be an acidic material present. Suitable for this purpose are any acids, and preferably those present in dry solid form. Especially appropriate are $C_2$–$C_{20}$ organic mono- and poly-carboxylic acids and especially alpha- and beta-hydroxycarboxylic acids; $C_2$–$C_{20}$ organophosphorus acids such as phytic acid; $C_2$–$C_{20}$ organosulfur acids such as toluene sulfonic acid; and peroxides such as hydrogen peroxide. Typical hydroxycarboxylic acids include adipic, glutaric, succinic, tartaric, malic, maleic, lactic, salicylic and citric acids as well as acid forming lactones such as gluconolactone and glucarolactone. Most preferred is citric acid. Also suitable as acid material may be encapsulated acids. Typical encapsulating material may include water soluble synthetic or natural polymers such as polyacrylates (e.g. encapsulating polyacrylic acid), cellulosic gums, polyurethane and polyoxyalkylene polymers. By the term "acid" is meant any substance which when dissolved in deionized water at 1% concentration will have a pH of less than 7, preferably less than 6.5, optimally less than 5. These acids preferably at 25° C. are in solid form, i.e. having melting points no less than 25° C. Concentrations of the acid should range from about 0.5 to about 80%, preferably from about 10 to about 65%, optimally from about 20 to about 45% by weight of the total composition.

For the effervescent type personal care cleansing compositions within the pouch, an alkaline material must be present. The alkaline material is a substance which can generate a gas such as carbon dioxide, nitrogen or oxygen, i.e. effervesce, when contacted with water and the acidic material. Suitable alkaline materials are anhydrous salts of carbonates and bicarbonates, alkaline peroxides (e.g. sodium perborate and sodium percarbonate) and azides (e.g. sodium azide). Preferably the alkaline material is sodium or potassium bicarbonate. Amounts of the alkaline material may range from about 1 to about 80%, preferably from about 5 to about 49%, more preferably from about 15 to about 40%, optimally from about 20 to about 35% by weight of the total composition.

By the term "substantially anhydrous" or "substantially dry" is meant the presence of no more than about 25%, preferably no more than about 10%, more preferably no more than about 5%, and optimally no more than 1% of water by weight of the composition or article, respectively. Water of hydration is not considered to be water for purposes of the anhydrous definition. However, it is preferred to minimize, preferably to eliminate any water of hydration.

Advantageously the combined amount of acidic and alkaline materials will be at least about 1.5%, preferably from about 40 to about 95%, optimally from about 60 to about 80% by weight of the total composition.

A variety of skin benefit agents may be included to improve afterfeel properties. Advantageously these substances will be available as substantially anhydrous dry powders. Alternatively these substances may be liquids deposited upon or into a powdered substrate (e.g. calcium silicate or zeolite) to achieve a resultant dry flowing powder. Within the skin benefit agent scope are several categories of materials. These include emollients, antiaging actives, antibacterials and fungicides, skin lighteners, sunscreens and combinations thereof. Amounts of the skin benefit agents may range from about 0.001 to about 40%, preferably from about 0.1 to about 20%, more preferably from about 0.5 to about 10%, optimally between about 1 and about 5% by weight of the total composition.

Emollients may be in the form of natural or synthetic esters, silicone oils, hydrocarbons, starches, fatty acids and mixtures thereof. Typically the emollient may range in concentration from about 0.1 to about 35% by weight of the total composition.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms.

Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C.

Among the ester emollients are:
(1) Alkenyl or alkyl esters of fatty acids having 10 to 22 carbon atoms. Examples thereof include isoarachidyl neopentanoate, isononyl isonanonoate, oleyl myristate, oleyl stearate, and oleyl oleate.
(2) Ether-esters such as fatty acid esters of ethoxylated fatty alcohols.
(3) Polyhydric alcohol esters. Ethylene glycol mono and di-fatty acid ester, diethylene glycol mono- and di-fatty acid esters, polyethylene glycol (200-8000) mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
(4) Wax esters such as beeswax, spermaceti, myristyl myristate, stearyl stearate and arachidyl behenate.
(5) Sterols esters, of which cholesterol fatty acid esters are examples thereof.
(6) Triglycerides such as sunflower seed oil, maleated sunflower seed oil, polycottonseedate, borage seed oil and safflower oil.

Hydrocarbons suitable as emollients include petrolatum, mineral oil, isoparaffins and hydrocarbon waxes such as polyethylene.

Starches are also suitable emollients. Typical of this class is tapioca and arabinogalactan.

Fatty acids may also be suitable as emollients. The fatty acids normally have from 10 to 30 carbon atoms. Illustrative of this category are pelargonic, lauric, myristic, palmitic, stearic, isostearic, hydroxystearic, oleic, linoleic, ricinoleic, arachidic, behenic and erucic acids.

Antiaging actives are also useful as skin benefit agents. Included within this category are vitamins, retinoids and combinations thereof. Amounts of these materials may range from about 0.001 to about 20% by weight of the total composition. Suitable vitamins include ascorbic acid, Vitamin $B_3$, Vitamin $B_6$, Vitamin $B_{12}$, tocopherol as well as salts and $C_1$–$C_{20}$ esters thereof. Suitable retinoids include retinoic acid as well as its $C_1$–$C_{22}$ esters and salts, retinol and $C_1$–$C_{22}$ fatty esters of retinol including retinyl linoleate.

Another class of antiaging actives are the alpha- and beta-hydroxycarboxylic acids and salts thereof. Representative of this group are glycolic acid, lactic acid, malic acid, hydroxyoctanoic acid, salicylic acid and mixtures of these as well as their salts. Suitable salts are the alkalimetal, ammonium and $C_1$–$C_{10}$ alkanol ammonium salts.

Antibacterials and fungicidals may also be included as skin benefit agents. Representative of these categories are triclosan, triclocarbon, hexetidene, chlorhexedene, gluconates, zinc salts (e.g. zinc citrate and zinc phenolsulfonate) and combinations thereof.

Skin lighteners may also be included under the skin benefit agents. Typical of this category are niacinamide, kojic acid, arbutin, vanillin, ferulic acid and esters thereof, resorcinol, hydroquinone, placental extract and combinations thereof.

Sunscreens may also be included as skin benefit agents. Particularly preferred are such materials as ethylhexyl p-methoxycinnamate, available as Parsol® MCX, avobenzene available as Parsol® 1789 and benzophenone-3, also known as Oxybenzone. Inorganic sunscreen actives may be employed such as microfine titanium dioxide, polyethylene and various other polymers. Amounts of the sunscreen agents may generally range from 0.1 to 30%, preferably from 2 to 20%, optimally from 4 to 10% by weight.

Adjunct functional agents may also be incorporated into compositions of the present invention. These include electrolytes, thickeners and mixtures thereof. Amounts of these substances may range from about 0.1 to about 20%, preferably from about 0.3 to about 10%, optimally between about 0.5 and about 5% by weight of the total composition.

Electrolytes may be selected from alkali, alkaline earth or ammonium salts of phosphates, silicates, halides, sulphates and mixtures thereof. Typical phosphates are potassium polymetaphosphate, sodium tripolyphosphate, sodium tetrapyrophosphate, sodium or potassium pyrophosphate and sodium hexametaphosphate. Most preferred is potassium polymetaphosphate available as Lipothix 100B® which is a 70:30 mixture of potassium polymetaphosphate and sodium bicarbonate, available from Lipo Chemicals, Inc., Paterson, N.J. Preferred sulphates are the magnesium sulphates.

Thickeners which may improve afterfeel properties on skin include inorganic or organic substances. A particularly preferred inorganic thickener is sodium magnesium silicate commercially available as Optigel SH®. Organic thickeners include alginic acid as well as sodium and calcium alginates, sodium carboxymethyl cellulose, hydroxypropyl methylcellulose, hydroxypropyl cellulose, hydroxyethyl cellulose and combinations thereof. Most preferred is alginic acid commercially available as Kelacid® from Sud-Chemie Rheologicals, Louisville, Ky. Alginic acid is highly effective at removing the slimy feel associated with deposits of alkaline material which are not fully rinsed away from the skin. Amounts of the thickener may range from about 0.1 to about 20%.

Polysaccharides useful in this invention are dry solid anhydrous substances such as sorbitol, sugars, (such as trehalose), starches, modified starches (e.g. aluminum octenyl succinate) and mixtures thereof. Most preferred is sorbitol.

Advantageously an emotive agent such as a fragrance and/or botanical extract are included with the effervescent cleansing composition. Fragrances and botanicals are often liquids. For this reason it may be necessary to uniformly distribute and allow absorption of liquid components into the solid powder. One method of best achieving this is to spray these liquids onto the solids. Amounts of the fragrance and/or botanicals combined may be at levels from about 0.1 to about 3%, preferably from 0.5 to 2%, optimally from 0.8 to 1.5% by weight of the total composition.

Colorants may also be included in compositions of the present invention. These substances may range from about 0.05 to about 5%, preferably between 0.1 and 3% by weight.

Except in the operating and comparative examples, or where otherwise explicitly indicated, all numbers in this description indicating amounts of material are to be understood as modified by the word "about".

The term "comprising" is meant not to be limiting to any subsequently stated elements but rather to encompass non-specified elements of major or minor functional importance. In other words the listed steps, elements or options need not be exhaustive.

The following examples will more fully illustrate embodiments of this invention. All parts, percentages and proportions referred to herein and in the appended claims are by weight unless otherwise indicated.

EXAMPLE 1

A personal care cleansing article of the effervescent type was prepared according to the following method with reference to the formulation reported in Table I. Phase A was dry blended in a high speed shearing mixer. Phase C was then formed by mixing mineral oil, Vitamin A palmitate, Vitamin E acetate, sunflower seed oil, green tea extract and fragrance, which combination was then sprayed with agitation onto calcium silicate. Thereafter Phase A and C were combined with mixing. Phase B was then incorporated with the other two phases and mixing continued for twenty minutes. The resultant dry blend was then fed into a Chilsonator® which processed the dry blend powder between high pressure rollers resulting in a compacted ribbon. A Fitz Mill was utilized to grind the ribbon into small particles. These particles were then sifted with the very fine and very large particles being recycled back into the Chilsonator®. Particles ranging in average size from about 75 to about 900 micron were separated and dosed at 2.9 grams to pouches. The pouches were formed from a layer of spun lace substrate and a second wall of SMS to which a high loft sheet was sealed. All sides of the pouch were welded by ultrasonic heat to ensure against powder escaping.

TABLE I

| Ingredient | Relative Weight |
| --- | --- |
| Phase A | |
| PEG 8000 | 5.00 |
| Sodium $C_{14-16}$ Olfein Sulfonate | 3.75 |
| Sodium Cocoyl Isethonate | 3.75 |
| Sodium Lauryl Sulfoacetate | 3.75 |
| Sodium Stearate | 3.00 |
| Disodium Dimethicone Copolyol Sulfosuccinate | 1.00 |
| Polyquaternium-7 | 0.50 |
| DL-Panthenol | 0.02 |
| Sodium Stearoyl Lactylate | 5.00 |
| Jaguar C-13 S ® | 3.00 |
| Phase B | |
| Sodium Bicarbonate | 24.00 |
| Citric Acid | 24.00 |
| Maltodextrin | 14.9 |
| Phase C | |
| Calcium Silicate | 7.00 |
| Mineral Oil | 4.00 |
| Vitamin A Palmitate | 0.01 |
| Vitamin E Acetate | 0.02 |
| Green Tea Extract | 0.20 |
| Sunflower Seed Oil | 0.01 |
| Fragrance | 0.50 |

EXAMPLE 2

A lather duration time (LDT) test was performed on the formulation reported in Table I, except that the levels of Jaguar C-13S® were varied from 0% to 7%. The test procedure was as follows.

A plastic tub (35 cm×25 cm) was positioned adjacent a sink. A bath mat with one approximately 1 cm width hole was placed into the tub with the smoother side (no ridges) facing upwards.

A cheesecloth (30 cm×25 cm) was folded to achieve a double layer. This cloth was placed over a 400 ml beaker. Both beaker and cloth were tared on a balance. The cheesecloth was then removed from the beaker and secured over another 400 ml beaker with a rubberband.

The personal care cleansing effervescent article of Example 1 was placed 6 inches from the faucet head of the sink. Water at 35–38 C and flow rate of 9000 ml/minute was allowed to wet the article for 5 seconds. The opposite side of the article was then wetted for another 5 seconds. The article was then placed into the plastic container on top of the bath mat and allowed to remain for 5 seconds.

The article was then gently tapped with a mixer head in an up and down motion for 15 seconds. Thereafter the article oriented at a 45 angle was rubbed by hand in a circular motion on the bath mat for 30 seconds. The side of the article being rubbed was alternated every 5 seconds. Excess lather was removed from fingers and hands directly onto the cheesecloth.

The bath mat was lifted allowing excess lather to be scraped from either side of the article with a spatula. All of the lather was gently transferred to the cheesecloth. Then the lather was scraped to the bottom of the plastic tub and the lather from the tub poured over the cheesecloth.

The cheesecloth was removed from beaker and draped over the other beaker which had previously been tared. Amount of lather on the cheesecloth was then recorded.

The article was re-wetted briefly on either side and allowed to remain on the bath mat for 5 seconds. The foregoing process was repeated beginning with the gentle tapping of the article with a mixer head. The re-wetting/lather cycle was continued until the non-woven no longer dispensed any lather.

Results of the tests are recorded in the Tables below.

| | Set 1 | | | |
| --- | --- | --- | --- | --- |
| | 0% | 3% | 5% | 7% |
| Jaguar % | (g) | (g) | (g) | (g) |
| 1 | 1.90 | 1.61 | 1.95 | 1.84 |
| 2 | 1.52 | 2.7 | 2.29 | 1.07 |
| 3 | 2.31 | 2.53 | 1.38 | 2.81 |
| 4 | 2.12 | 3.35 | 2.3 | 2.12 |
| 5 | 1.92 | 2.44 | 1.12 | 2.16 |
| 6 | 0 | 2.00 | 1.40 | 2.59 |
| 7 | | 2.25 | 1.42 | 1.60 |
| 8 | | 2.18 | 1.93 | 2.44 |
| 9 | | 2.21 | 0.92 | 3.42 |
| 10 | | 2.50 | 0.01 | 2.29 |
| 11 | | 2.86 | 0 | 1.91 |
| 12 | | 1.60 | | 1.89 |
| 13 | | 0.01 | | 1.67 |
| 14 | | 0 | | 0.01 |
| 15 | | | | 0 |

| Jaguar % | Set 2 | | | |
|---|---|---|---|---|
| | 0% (g) | 3% (g) | 5% (g) | 7% (g) |
| 1 | 2.44 | 1.49 | 1.95 | 1.81 |
| 2 | 3.13 | 1.83 | 2.19 | 2.77 |
| 3 | 2.16 | 1.90 | 2.30 | 2.82 |
| 4 | 2.63 | 1.44 | 1.95 | 2.07 |
| 5 | 2.67 | 1.59 | 1.59 | 2.56 |
| 6 | 3.04 | 1.50 | 1.88 | 4.10 |
| 7 | 1.18 | 1.61 | 2.34 | 2.28 |
| 8 | 0 | 1.31 | 3.32 | 3.03 |
| 9 | | 1.31 | 1.49 | 3.32 |
| 10 | | 0.93 | 1.62 | 3.38 |
| 11 | | 0.50 | 1.81 | 3.10 |
| 12 | | 0 | 1.37 | 2.87 |
| 13 | | | 1.03 | 2.72 |
| 14 | | | 1.27 | 3.05 |
| 15 | | | 0.67 | 3.23 |
| 16 | | | 0.01 | 2.78 |
| 17 | | | 0 | 2.25 |
| 18 | | | | 1.28 |
| 19 | | | | 0 |

| Jaguar % | Set 3 | | | |
|---|---|---|---|---|
| | 0% (g) | 3% (g) | 5% (g) | 7% (g) |
| 1 | 1.65 | 1.83 | 2.38 | 1.33 |
| 2 | 1.91 | 2.45 | 2.03 | 1.34 |
| 3 | 2.14 | 1.91 | 2.11 | 1.04 |
| 4 | 2.81 | 1.85 | 2.16 | 1.06 |
| 5 | 1.40 | 2.01 | 2.36 | 1.75 |
| 6 | 0.50 | 3.11 | 2.50 | 3.07 |
| 7 | 0 | 2.03 | 1.50 | 1.47 |
| 8 | | 1.95 | 2.60 | 1.52 |
| 9 | | 2.44 | 2.45 | 2.31 |
| 10 | | 1.61 | 2.15 | 1.92 |
| 11 | | 0.10 | 2.54 | 2.88 |
| 12 | | 0 | 1.51 | 2.64 |
| 13 | | | 2.69 | 1.53 |
| 14 | | | 0.01 | 0.50 |
| 15 | | | 0 | 0 |
| 16 | | | | |

Each set represents a repeat evaluation. The results recorded in the Tables above demonstrate a steady increase of lather duration time as the Jaguar concentration rises from 3 to 7%. Indeed, the increased duration is almost twice as much as found in the 0% formula.

EXAMPLE 3

Another personal care cleansing article of the effervescent type is prepared having the composition reported in Table II. Phase A is dry blended in a high speed shearing mixer. Fragrance is then sprayed onto the resultant powder as a Phase B. Only those particles with average particle size from 75 to 900 micron are employed for the cleansing composition. These are separated by sifting through a set of wire screens. Three grams of the selected sifted powder are then placed into a 5 by 7.5 cm square pouch formed of non-woven rayon/polyester. All sides are closed by thermal heat sealing.

TABLE II

| Ingredient | Relative Weight |
|---|---|
| PHASE A | |
| Sodium Bicarbonate | 33.6 |
| Citric Acid (Anhydrous) | 39.0 |
| Sodium Cocoyl Isethionate (Powder) | 3.0 |
| Sodium Methyl Cocoyl Taurate | 6.0 |
| Sodium Lauryl Sulfate | 2.5 |
| Sodium Sesquicarbonate | 5.0 |
| Lipotbix 100B ® (Potassium Polymetaphosphate/Bicarbonate 70:30) | 0.5 |
| Optigel SH ® (Sodium Magnesium Silicate) | 2.0 |
| Tapioca | 1.75 |
| Methyl Gluceth 20-Benzoate | 2.0 |
| Guar Hydroxypropyl Trimonium Chloride | 4.0 |
| PHASE B | |
| Fragrance | 0.65 |

EXAMPLE 4

This Example presents experiments correlating average particle size with foam enhancement. These experiments utilized the formulation reported in Table I except that levels of Jaguar C-13S® were varied between 0 to 7% by weight.

The personal care cleansing articles of Example 1 were held at 15 cm from a faucet head of a sink. Water at 35–38 C and at a flow rate of 9,000 ml/minute were allowed to wet the article for 5 seconds on one side. The opposite side was then wetted for an additional 5 seconds. Thereafter the article was transferred to a small plastic tray and placed under an Instron® model 4501 tester.

The Instron 4501® was set for speed of 250 mm/minute and settings were made at −21 mm and touch set 6.1. The work utilized to deflate the article (i.e. billowed pouch) at a set distance was calculated by integrating an area under a force vs. distance curve generated by the Instron®. Results are reported in Table III.

TABLE III

Jaguar % at Various Particle Sizes Vs Work to Deflate

| Average Particle Size (Micron) | Jaguar ® Weight % Work (kg × mm) | | | |
|---|---|---|---|---|
| | 0% | 3% | 5% | 7% |
| 850 | 2.86 | 3.75 | 4.34 | 8.55 |
| 450 | 3.81 | 10.26 | 12.73 | 17.30 |
| 180 | 5.20 | 9.18 | 11.21 | 15.02 |
| 125 | 3.33 | 5.91 | 6.84 | 12.17 |
| 75 | 3.14 | 5.01 | 5.15 | 7.86 |

Based on the results obtained as shown in Table III, foam enhancement occurs in the range between 75 and 850 micron range. Optimum results can be found in the range from 180 to 450 micron.

The foregoing description illustrates selected embodiments of the present invention. In light thereof, variations and modifications will be suggested to one skilled in the art, all of which are within the spirit and purview of this invention.

What is claimed is:

1. A substantially dry personal care cleansing article comprising:
   (i) a water insoluble substrate;
   (ii) a personal care composition adjacent the substrate, which includes:
      (a) from about 0.5 to about 60% of at least one lathering surfactant by weight of the composition;
      (b) from about 2 to about 15% of a cationic polymer by weight of the composition; and
      (c) a carrier for the lathering surfactant and cationic polymer, the composition having an average particle size ranging from about 75 to about 900 micron.

2. The article according to claim 1 wherein the average particle size ranges from about 100 to about 500 micron.

3. The article according to claim 1 wherein the substrate forms a sealed pouch enclosing an effervescent powdered composition.

4. The article according to claim 1 wherein the cationic polymer is a cationic polysaccharide.

5. The article according to claim 4 wherein the cationic polymer is guar hydroxypropyl trimonium salt.

6. The article according to claim 1 wherein the cationic polymer is present in an amount from about 3 to about 10% by weight of the composition.

7. The article according to claim 1 wherein the water-insoluble substrate relative to that of the composition ranges in weight from about 20:1 to about 1:20.

* * * * *